(12) United States Patent
Kramer et al.

(10) Patent No.: US 9,173,965 B2
(45) Date of Patent: Nov. 3, 2015

(54) DEVICE AND METHOD FOR MEASURING AN ANALYTE UNDER THE NAIL

(71) Applicants: Marcus A. Kramer, Circle Pines, MN (US); Rush L. Bartlett, II, Mountain View, CA (US)

(72) Inventors: Marcus A. Kramer, Circle Pines, MN (US); Rush L. Bartlett, II, Mountain View, CA (US)

( * ) Notice: Subject to any disclaimer, the term of this patent is extended or adjusted under 35 U.S.C. 154(b) by 0 days.

(21) Appl. No.: 14/172,897

(22) Filed: Feb. 4, 2014

(65) Prior Publication Data

US 2014/0155718 A1    Jun. 5, 2014

Related U.S. Application Data

(63) Continuation of application No. PCT/US2012/050114, filed on Aug. 9, 2012.

(60) Provisional application No. 61/521,551, filed on Aug. 9, 2011, provisional application No. 61/620,607, filed on Apr. 5, 2012.

(51) Int. Cl.
| A61B 5/1455 | (2006.01) |
| A61K 49/00 | (2006.01) |
| A61B 5/00 | (2006.01) |
| A61B 5/145 | (2006.01) |

(52) U.S. Cl.
CPC ............ *A61K 49/0002* (2013.01); *A61B 5/1455* (2013.01); *A61B 5/449* (2013.01); *A61B 5/6826* (2013.01); *A61B 5/145* (2013.01); *A61B 5/14532* (2013.01)

(58) Field of Classification Search
CPC ..................... A61B 5/1455; A61B 2562/0233; A61B 2562/0238
USPC ................................. 600/310, 322, 344, 335
See application file for complete search history.

(56) References Cited

U.S. PATENT DOCUMENTS

| 5,827,181 | A | * | 10/1998 | Dias et al. | 600/322 |
| 6,032,070 | A | * | 2/2000 | Flock et al. | 600/310 |
| 6,466,807 | B1 | * | 10/2002 | Dobson et al. | 600/316 |
| 7,577,469 | B1 | * | 8/2009 | Aronowitz et al. | 600/310 |
| 2006/0224058 | A1 | * | 10/2006 | Mannheimer | 600/323 |

* cited by examiner

Primary Examiner — Eric Winakur
(74) Attorney, Agent, or Firm — Frost Brown Todd LLC

(57) ABSTRACT

An apparatus includes a source and a detector. The source is operable to transmit light. The detector is operable to receive at least a portion of the light transmitted by the source. The source and the detector can be positioned on a nail of a digit such that the light enters the nail through an entrance region. The light further exits the nail through an exit region. The entrance region is defined by a lateral portion of the nail. The light is directed to interact with at least one analyte.

2 Claims, 16 Drawing Sheets

DEVICE AND METHOD FOR MEASURING AN ANALYTE UNDER THE NAIL

PRIORITY

This application is a continuation of and claims priority to international application PCT/US12/50114, filed Aug. 9, 2012, entitled "DEVICE AND METHOD FOR MEASURING AN ANALYTE UNDER THE NAIL"; this application also claims priority to U.S. Provisional Patent Application Ser. No. 61/521,551, filed Aug. 9, 2011, entitled "Noninvasive Measurement of Analyte(s) under Nail Using Lateral Electromagnetic Measurement Methods and Apparatus," and to U.S. Provisional Patent Application Ser. No. 61/620,607, filed Apr. 5, 2012, entitled "Noninvasive Measurement of Analyte(s) under the Nail: Methods and Apparatus," the disclosures of which are incorporated by reference herein.

BACKGROUND

Non-invasive measurement of body chemistry holds significant promise for a broad segment of the population, such as for example, diabetics. Also included are individuals and medical professionals interested in non-invasively monitoring other organic and/or inorganic compounds as they relate to natural functioning physiology or disease states of the body. More than 200 million people worldwide and approximately 23.7 million Americans are suffering with diabetes. In America diabetics are advised to have blood drawn as often as five to seven times per day to adequately monitor their insulin treatments. Understandably, patients in any situation of which a blood analyte test is required do not enjoy having their blood drawn but this is critical in the daily testing required by diabetics. This inconvenience may lead to a lack of testing and therefore a lack of compliance with disease treatments further enhancing the spread and/or progression of a disease such as but not limited to diabetes. For instance, in other scenarios, it may be necessary for an individual to monitor other analytes such as urea, cholesterol, triglycerides, total protein, albumin, hemoglobin, hematocrit, bilirubin, or any other suitable analyte. Furthermore, other analytes may be of interest depending on the individual situations of the patient.

The current clinically accepted method of analyzing blood chemistry involves removing a blood sample by puncturing the skin with a needle. The sample is then tested for one of a number of compounds contained within the blood that provides information about a physiological condition or function. For diabetics, the tests are performed on disposable test strips which create a large financial obligation for patients over their lifetime. Beyond the immediate pain and discomfort many diabetics show reluctance to test for concern over the possibility of infection, discomfort, cultural pressure and generalized patient fear.

While a variety of analyte testers have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
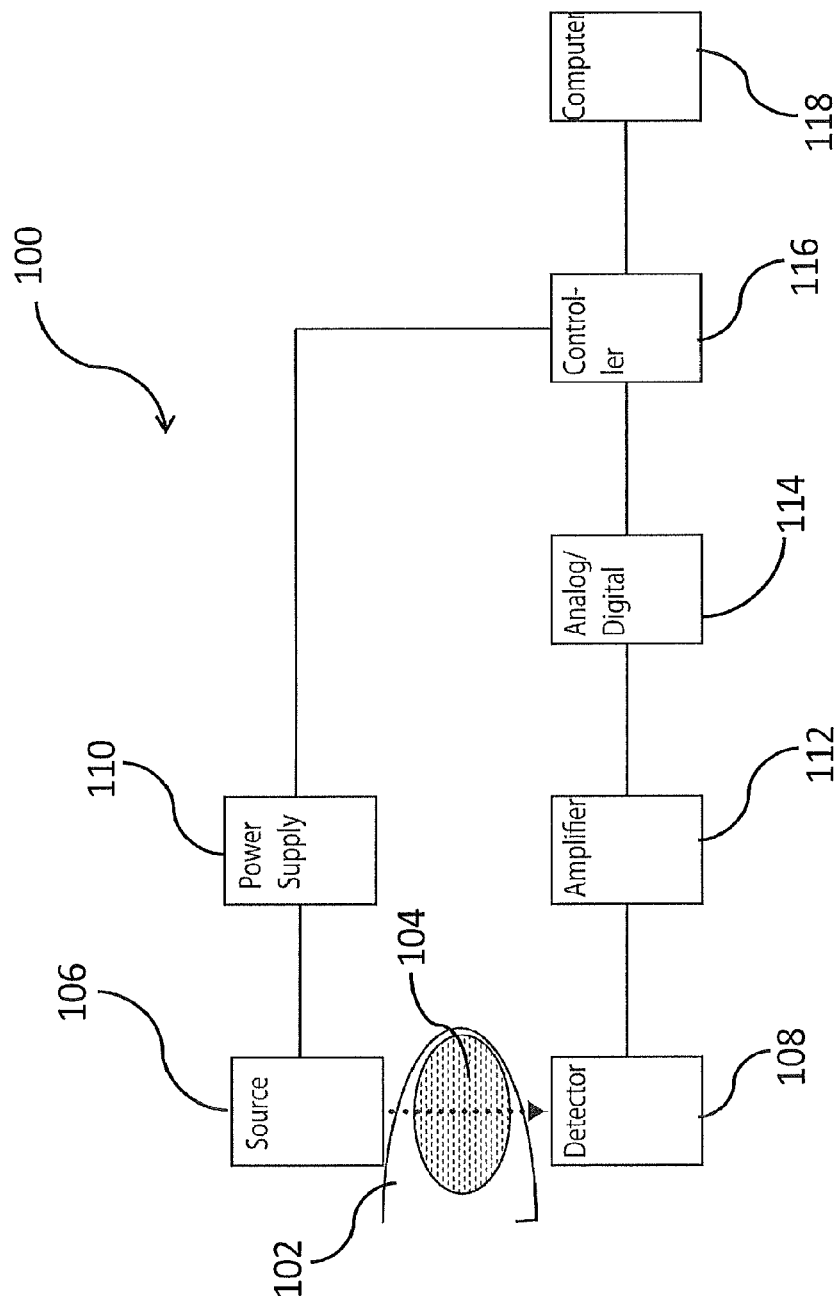
FIG. 1 depicts a diagrammatic view of an exemplary analyte tester.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIG. 1 illustrates an exemplary analyte tester (100). Generally speaking, analyte tester (100) may be used to detect an analyte within a patient or user non-invasively. In one exemplary version, analyte tester (100) may be placed onto a region of the user such as one or more fingernails for detecting the presence of or a level of concentration of an analyte through the nail. Thereafter, the reading from analyte tester (100) may be transmitted to another machine such as a computer for output or recordation of the reading. In some instances, analyte tester (100) may be integrated with a computer or computing device into a single machine. Further details regarding several exemplary versions will be discussed below.

In FIG. 1, analyte tester (100) comprises a source (106) and a detector (108). Source (106) is operable to transmit a signal or light beam to detector (108) through the nail (104) of a user's finger (102). In the illustrated version, source (106) is positioned opposing detector (108) such that finger (102) is between source (106) and detector (108). However, it will be appreciated that other configurations may be used as well, which will be discussed in further detail below.

Source (106) may comprise any suitable signal generating source as would be apparent to one of ordinary skill in the art in view of the teachings herein. In particular, the exemplary version shows source (106) that is operable to deliver electromagnetic radiation to nail (104) to be detected by detector (108). In other exemplary versions, other types of signal may be transmitted by source (106) where source (106) is operable to transmit a signal through nail (104) to reach detector (108). The signal may include any suitable light or wave beam operable to travel through nail (104). Source (106) may further be configured to fire a beam through a channel prior to entering the nail or source (106) may simply fire a beam directly into nail (104). Similarly, detector (108) may be operable to receive a beam from source (106) either directly after having passed through nail (104) or through a channel or through any other suitable means. Further details regarding the orientation of source (106) and detector (108) for transmission of signal through nail (104) will be discussed in further detail below.

In one exemplary version, source (106) is operable to produce a near infrared ("NIR") beam to be transmitted to detector (108) by firing NIR through nail (104). It will be appreciated that the NIR may potentially include signals having various wavelengths such as between approximately 2000-2500 nm (hereinafter referred to as "the combination"), approximately 1333-1818 nm (hereinafter referred to as "the first overtone"), and approximately 700-1176 nm (hereinafter referred to as "the short wavelength"). It will be appreciated that in some versions, the combination and the first overtone may be used as the specifications for generating a beam by source (106). However, it will be understood that any suitable spectral length may be used as would be apparent to one of ordinary skill in the art. For instance, the combination may be used; the first overtone may be used; the short wavelength may be used; and combinations thereof may be used. In yet other versions, wavelengths outside of the above mentioned wavelength ranges may be used as well. It will further be understood that the beam fired between source (106) and detector (108) may be between 1-5 mm, but of course, any suitable distance between source (106) and detector (108) may be used as would be apparent to one of ordinary skill in the art. In fact, a longer or short path length for the beam may be used. Furthermore, it will be appreciated that the above-mentioned parameters may be used when analyte tester (100) is used, for instance, in predicting blood glucose concentration. Of course, the same, similar, or even different parameters may be used when attempting to determine the concentration of other analytes.

It will further be appreciated that while analyte tester (100) may be used in one version to detect analytes, analyte tester (100) may also be used to determine physiological, pathological, or other biologically induced changes. For instance, source (106) of analyte tester (100) could fire multiple beams toward detector (108) in succession resulting in a series of measurements regarding information about the beam based on how the beam absorbs, transmits, refracts, scatters, or reflects through blood in finger (102). Once such information is acquired, the user or another party may be able to determine physiological traits based on the rate of change of such information. For instance, changes in blood volume due to pulsation of blood within finger (102) or other digit may be detected by determining the rate of change of transmission of a beam through finger (102). In yet other exemplary instances, conditions such as sickle cell anemia could be detected as a result of firing a beam laterally through finger (102) and observing or detecting changes in the scattering of light through finger (102) as detected by detector (108). Thus, while in some instances, it is contemplated that blood glucose may be determined using analyte tester (100), other analytes or even physiological, pathological, or biologically induced changes may be detected as well as would be apparent to one of ordinary skill in the art in view of the teachings herein.

It will further be appreciated that source (106) may be equipped or in communication with a collimator operable to narrow or focus a beam, particles, signal, waves, etc. being transmitted by source (106). The collimator may be integrally formed with source (106), or may be a separate component in communication with source (106). Other suitable variations will be apparent to one of ordinary skill in the art in view of the teachings herein.

Source (106) is in communication with power supply (110) such that power supply (110) is operable to provide sufficient power to source (106) to transmit a beam or other signal through nail (104) to detector (108). For instance, source (106) may be configured to receive AC, DC or any other suitable type of power from power supply (110). Power supply (110) in the illustrated version is in communication with a controller (116). Controller (116) is operable to control the operation of power supply (110), which may include turning on power supply (110) and/or directing power supply (110) to deliver a particular type of power. It will also be appreciated that controller (116) may be in communication through power supply (110) to direct source (106) to deliver a particular type of signal. It will also be understood that power supply (110) need not necessarily connect directly to controller (116). Other suitable configurations will be apparent to one of ordinary skill in the art in view of the teachings herein.

As stated above, source (106) transmits one or more signals and/or beams to detector (108) through nail (104). Detector (108) is in communication with an amplifier (112) such that signal received by detector (106) may be amplified. In some exemplary versions, in addition to amplifying signal, amplifier (112) may be operable to filter signal prior to amplifying it. It will be appreciated that other suitable variations may be used as would be apparent to one of ordinary skill in the art.

Amplifier (112) is in communication with an analog/digital converter ("ADC") (114) such that the signal received by ADC (114) may be converted for use by a controller (116) and/or computer (118). Controller (116) is operable to control the operation of any of the components of analyte tester (100). Controller (116) may then be operable to send received data to computer (118), where computer (118) can store, display, or otherwise process information received from detector (108). Computer (118) may, for instance, perform any suitable multivariate analysis that may be operable to determine the amount of analyte in finger (102) based on the spectral signal received by detector (108). While in the illustrated version, controller (116), computer (118), ADC (114), and amplifier (112) are shown as separate components, it will be appreciated that they may be integrated into a single unit for use with analyte tester (100).

Figure 2:
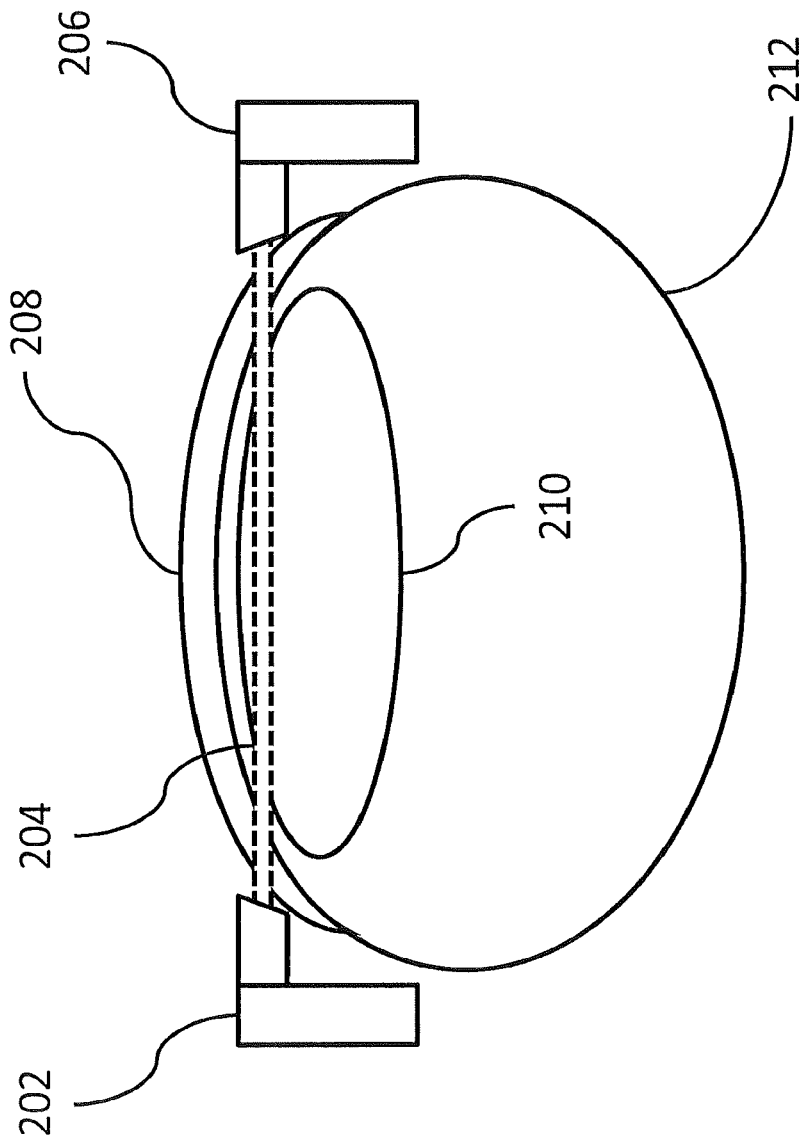
FIG. 2 depicts a front partially cross sectional view of the source and detector of FIG. 1 positioned on the nail of a finger.

FIG. 2 shows an exemplary source (206) and detector (202) of analyte tester (100) oriented for use on a finger (212). In some versions, finger (212) may be selected as the index finger, but it will be understood that source (206) and detector (202) may be used with any suitable finger (212). Furthermore, in some instances, source (206) and detector (202) may be used with any digit of the body including fingernails as well as toenails. Indeed, it will be understood that source (206) and detector (202) of analyte tester (100) may be used on any portion of the body that exhibits similar transmission characteristics as a nail.

As can be seen in FIG. 2, source (206) and detector (202) are positioned such that light beam (204) travels across a secant of the nail (208). In particular, source (206) is laterally positioned such that beam (204) enters through a side portion of nail (208). As seen in the illustrated version, source (206) is positioned such that the initial firing path of beam (204) defines a secant with the curvature of nail (208). It will be understood that source (206) may be located at any suitable position away from the top-center of nail (208) and along the side of nail (208) that allows source (206) to fire beam (204) laterally and/or horizontally through nail (208). As can also be seen, as beam (204) passed through nail (208), beam (204) also encounters a sterile matrix (210) within nail (208). It will be understood that sterile matrix (210) contains an analyte that beam (204) or portions of beam (204) hits when beam (204) travels through nail (208). Upon contacting matrix (210) or an analyte contained within matrix (210), it will be appreciated that beam (204) may interact with an analyte. After beam (204) enters nail (208), travels through matrix (210), interacts with an analyte, and exits nail (208), beam (204) then is received by detector (202). It will be appreciated that as beam (204) hits one or more analytes contained in matrix (210), a portion of beam (204) may be reflected, refracted, scattered, re-emitted or otherwise affected by an analyte or other component contained within matrix (210) such that the portion of beam (204) received by detector (202) reflects information that can be used to determine the presence of or the concentration of analyte contained within matrix (210). Beam (204) information received by detector (202) may then be used or otherwise processed by, for instance, amplifier (112), ADC (114), controller (116), computer (118) as was shown in FIG. 1. For instance, beam (204) may result in a signal received by detector (202), which is amplified, converted, then processed by controller (116) and/or computer (118).

As also seen in FIG. 2, source (206) and detector (202) are oriented such that they are positioned horizontally and/or laterally across nail (208). While the illustrated version shows source (206) and detector (202) opposing each other directly, it will be appreciated that other lateral orientations may be used as well, which will be discussed in further detail below. As also seen in FIG. 2, source (206) and detector (202) contact nail (208). In other versions, source (206) and detector (202) may be positioned such that there is an air gap between source (206) and nail (208) and/or between detector (202) and nail (208). In yet other versions, an adhesive, gel, or other substance may be used between source (206) and nail (208) and/or between detector (202) and nail (208). In some instances, the adhesive or gel used may be operable to adhere source (206) and/or detector (202) to nail (208), and in some instances, the adhesive or gel may be used to facilitate transmission of beam (204) from source (206) or detector (202) to nail (208).

Figure 3:
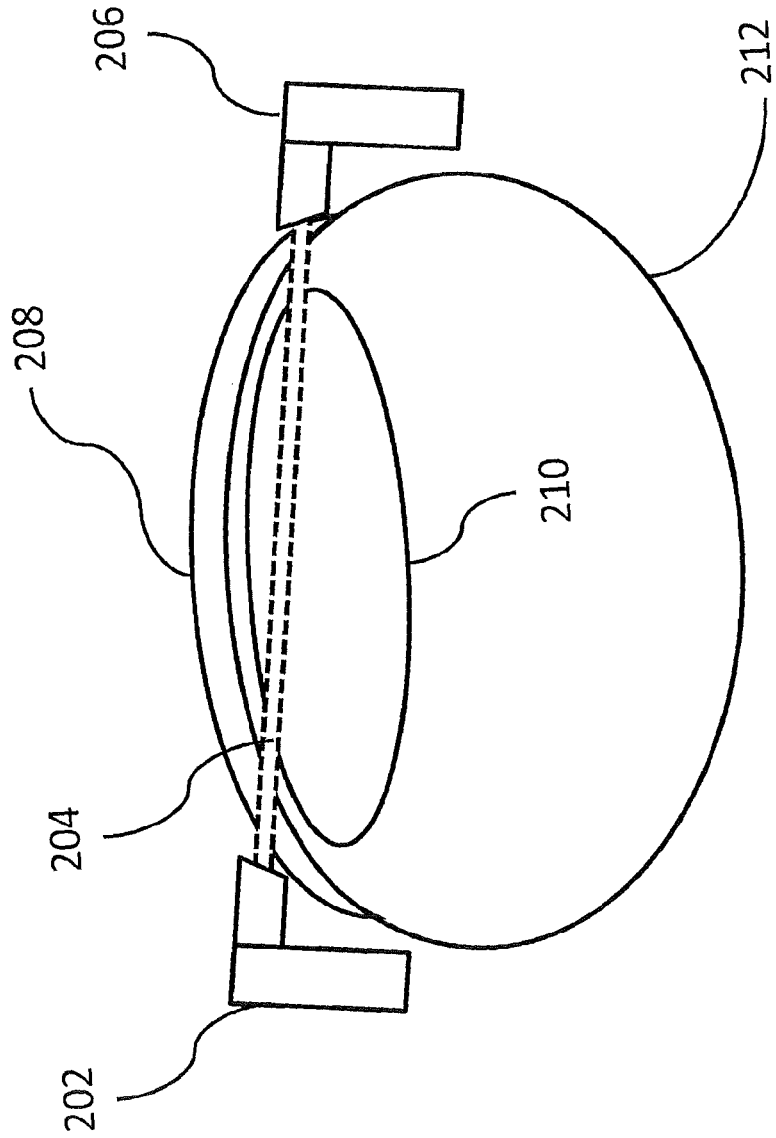
FIG. 3 depicts a front partially cross sectional view of the source and detector of FIG. 2 positioned on the nail of a finger at an oblique angle.

FIG. 3 shows another merely exemplary orientation for source (206) and detector (202) where source (206) and detector (208) are positioned such that beam (204) still defines a secant across nail (208), but beam (204) sits slightly oblique along nail (208). As shown in the illustrated version, source (206) still is positioned such that beam (204) enters nail (208) through a side or lateral portion of nail (208). It will be appreciated that source (206) and detector (202) may be moved between the positions shown in FIG. 2 and FIG. 3 as needed by the user or to other suitable positions as would be apparent to one of ordinary skill in the art in view of the teachings herein.

Figure 4:
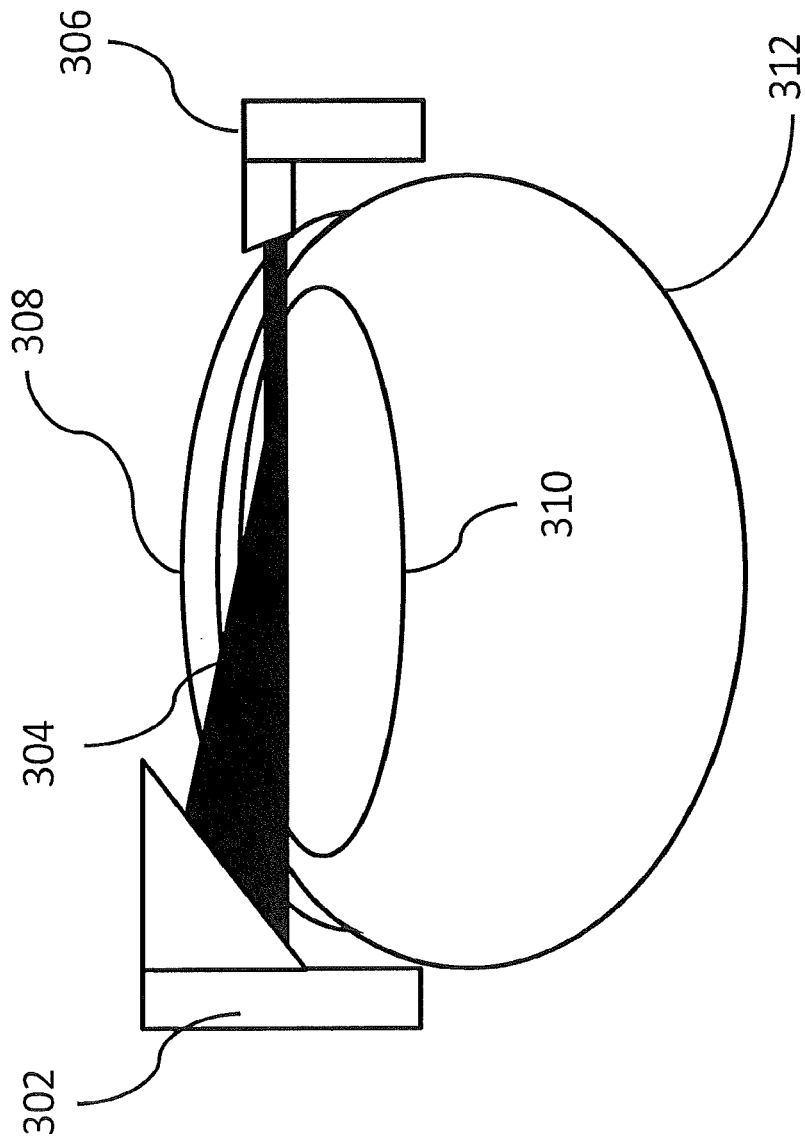
FIG. 4 depicts a front partially cross sectional view of an alternative exemplary version of a source and an enlarged detector positioned on the nail of a finger.

FIG. 4 shows an alternative exemplary version of source (306) and detector (302) for use on a finger (312) having a nail (308) where a beam (304) is passed through nail (304). Beam (304) travels through a matrix (310). As beam (304) travels through matrix (310) it will be appreciated that one or more analytes or other components in matrix (310) may absorb, transmit, or re-emit a portion of beam (304). In the illustrated version, source (306) is substantially similar to sources shown, for instance, in FIGS. 1-3. Source (306) directs beam (304) laterally through nail (308). It will be appreciated that in some instances, a portion of beam (304) may refract as shown in FIG. 4. Accordingly, detector (302) may be larger such that detector (302) can receive portions of beam (304) as beam (304) is transmitted, scattered, refracted, reflected, or absorbed and subsequently emitted by an analyte or other component in matrix (310).

Figure 5:
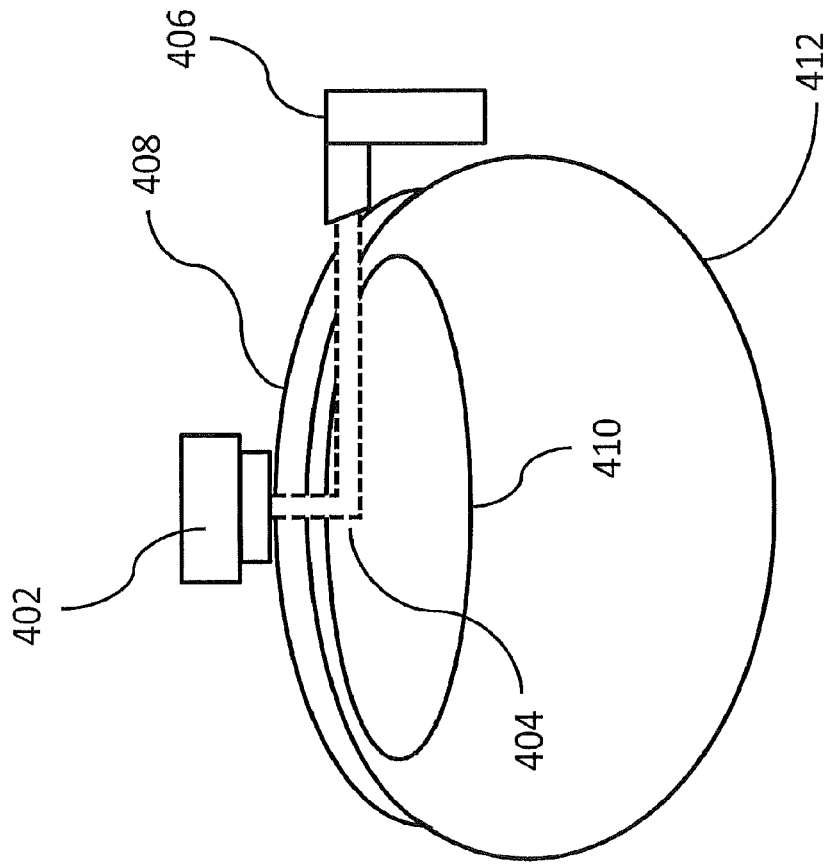
FIG. 5 depicts a front partially cross sectional view of yet another alternative exemplary version of a source and a detector positioned at the top of a nail of a finger.

FIG. 5 shows yet another exemplary configuration of source (406) firing a beam (404) laterally into the matrix (410) under a nail (408) of a finger (412). In the illustrated version, detector (402) is positioned at the top of nail (408) such that detector (402) can detect and/or measure any portion of beam (404) that refracts, scatters, is absorbed and emitted upwards, or otherwise reflects upward. In the illustrated version, detector (402) is positioned at the center at the top of nail (408), but it will be appreciated that detector (402) may be positioned at any point along nail (408) to detect light from beam (404) after laterally entering nail (408).

Figure 6:
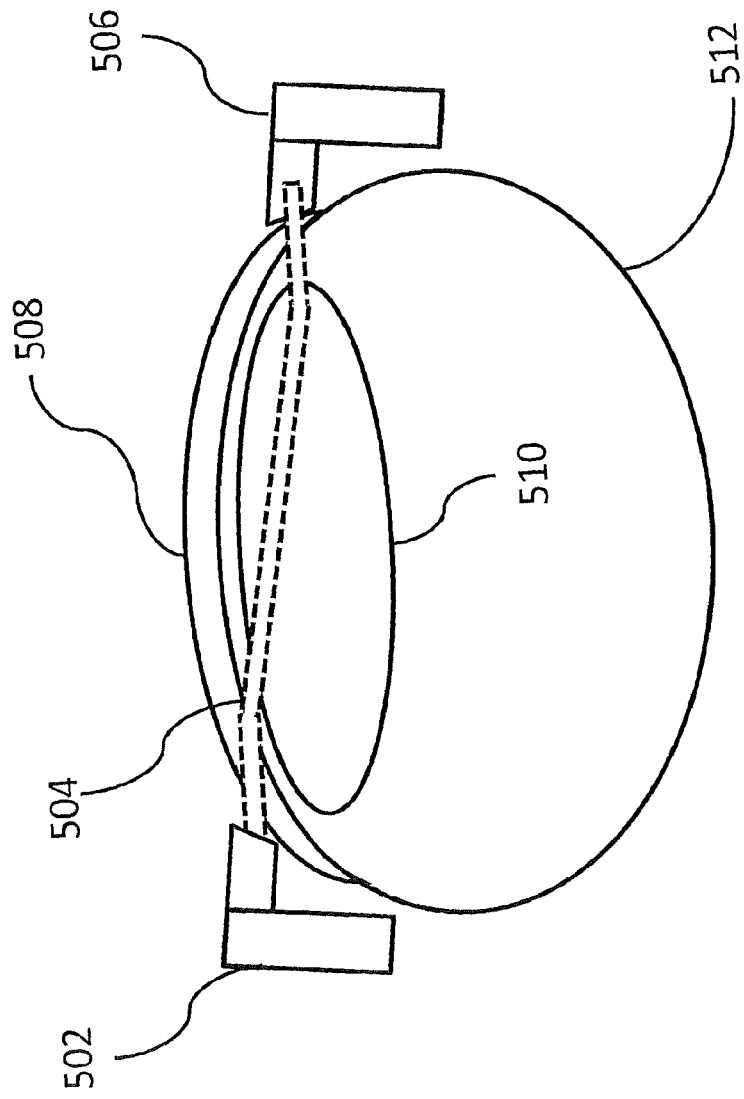
FIG. 6 depicts a front partially cross sectional view of yet another alternative exemplary version of a source and a detector positioned at an oblique angle along nail.

FIG. 6 shows another exemplary version of a source (506) and detector (502) for use with a nail (508) of a finger (512) where a matrix (510) contains one or more analytes and where a beam (504) is directed through matrix (510) from source (506) to detector (502). In the illustrated version, detector (502) is positioned such that detector (502) can detect or receive beam (504) that has been refracted through matrix (510) after beam (504) has traveled a somewhat crooked path to reach detector (502).

Figure 7:
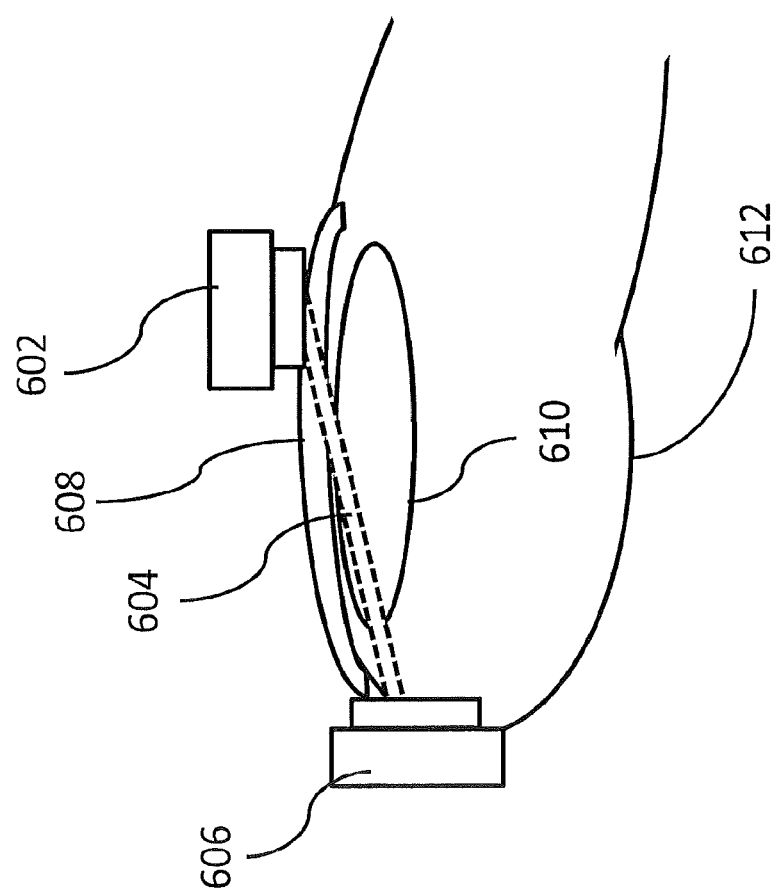
FIG. 7 depicts a side elevation view of yet another alternative exemplary version of a source and a detector with the source positioned at the front of the finger.

FIG. 7 shows an alternative exemplary set up for source (606) and detector (602) where source (606) is positioned at the end of the finger (612) and detector (602) is positioned around the top of the nail (608). Source (606) transmits a beam (604) through the finger (612), through a matrix (610) such that beam (604) exits the nail (608) and is received by detector (602). While in the illustrated version, source (606) is positioned such that beam (604) enters finger (612) slightly below nail (608) it will be appreciated that source (606) could be positioned slightly higher such that source (606) passes through nail (608) first before entering matrix (610). As previously mentioned, while the illustrated version shows source (606) and detector (602) being used with finger (612), it will be appreciated that source (606) and detector (602) may be used with any digit including any finger and/or any toe.

Figure 8:
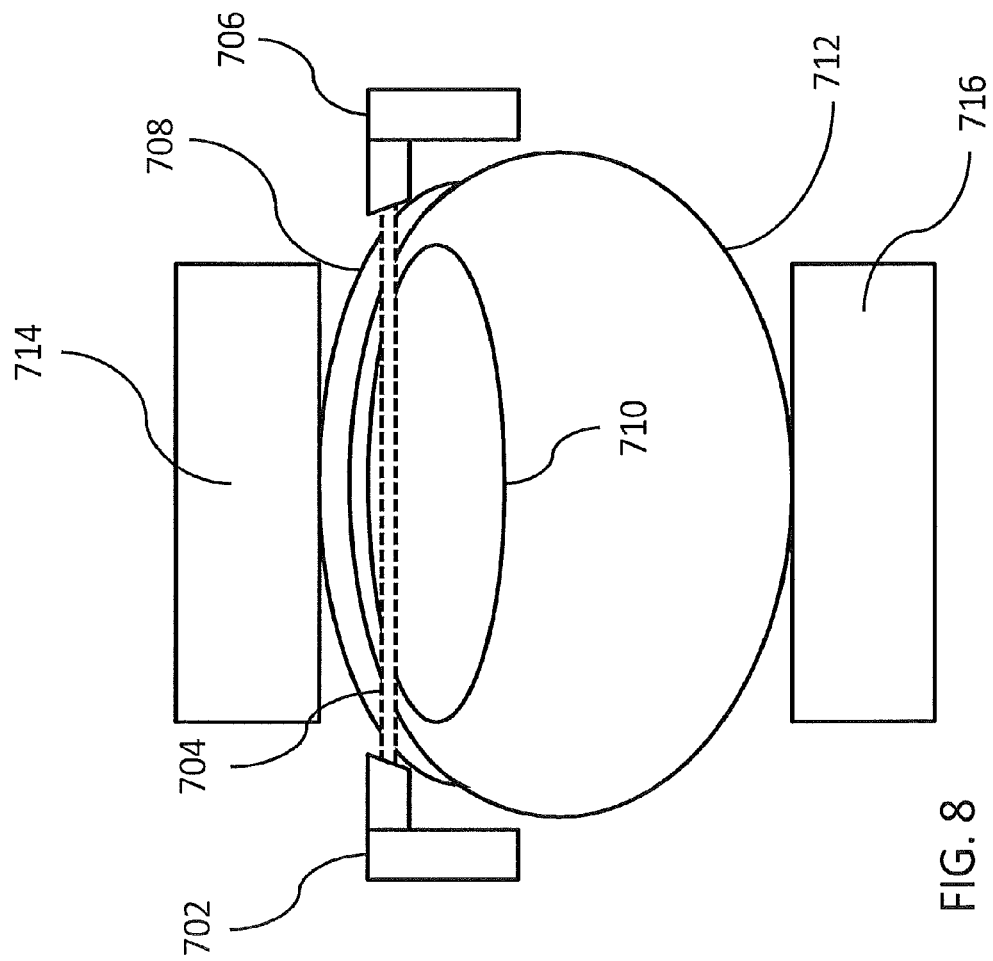
FIG. 8 depicts a front partially cross sectional view of yet another alternative exemplary version of a source and a detector with one or more compression plates.

FIG. 8 shows an alternative setup where source (706) and detector (702) are positioned to transmit beam (704) through nail (708) of finger (712). As beam (704) is fired through finger (712), beam (704) passes through matrix (710). Compression plates (714, 716) may be placed around finger (712). Top compression plate (714) may be placed directly on nail (708) or may be placed with an adhesive, liquid, or other suitable substance between top compression plate (714) and nail (708). Bottom compression plate (716) may similarly be positioned against the bottom of finger (712) as seen in FIG. 8. In some versions, it will be understood that a liquid, adhesive, or other substance may be placed in between bottom compression plate (716) and finger (712) to further facilitate contact between bottom compression plate (716) and finger (712).

It will be appreciated that use of compression plates (714, 716) may have several effects on readings received by detector. For instance, compressing finger (712) may remove a portion of blood from the finger (712) region thereby allowing better signal penetration. Compressing finger (712) may also provide differential readings between a compressed and uncompressed state of finger (712). Finally, it will also be appreciated that compressing finger (712) may decrease the level of background noise associated with any readings from finger (712).

Figure 9:
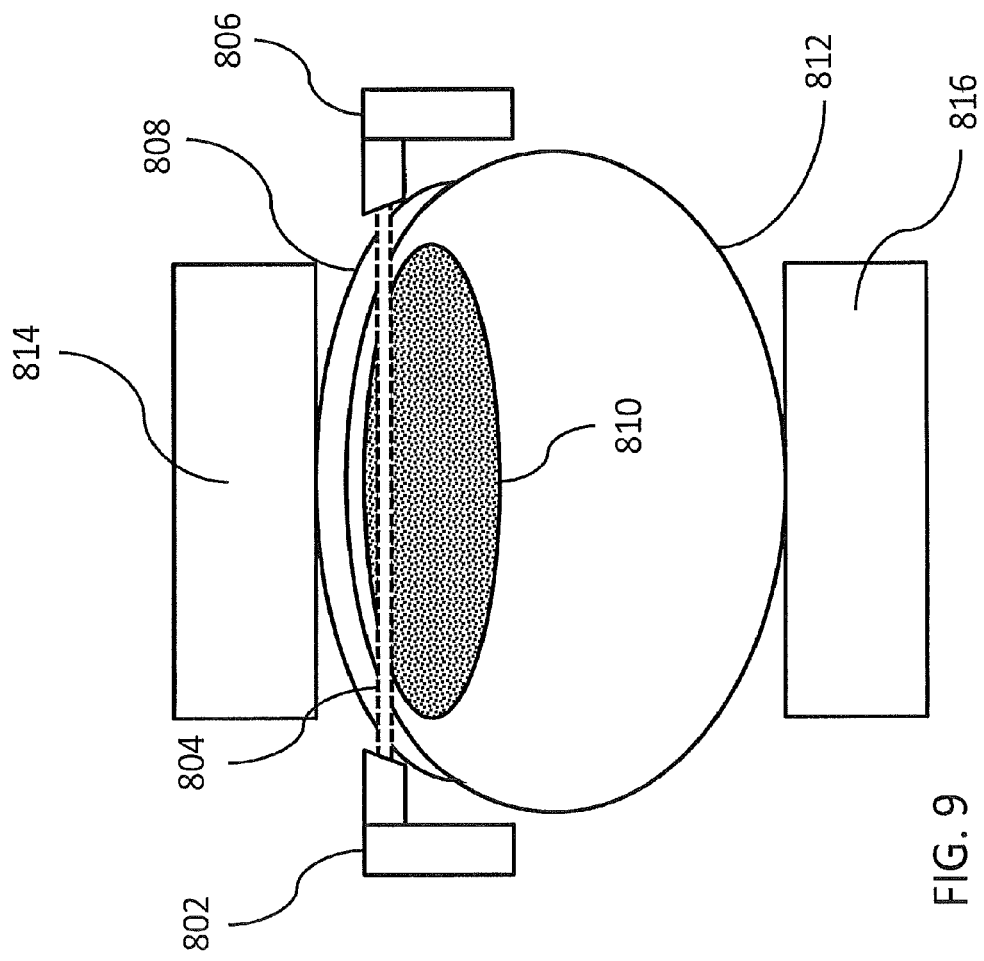
FIG. 9 depicts a front partially cross sectional view of yet another alternative exemplary version of a source and a detector with one or more compression plates with an agent in the matrix of the finger.

FIG. 9 shows an alternative configuration for use of source (806) and detector (802) where source (806) transmits a beam (804) through nail (808) of finger (812). As beam (804) enters nail (808), beam (804) also passes through matrix (810). In the illustrated version, matrix (810) is a modified matrix due to the patient ingesting a substance or medicament that enhances the detectability of an analyte in matrix (810). For instance, as beam (804) passes through matrix (810), beam (804) interacts with the reagent contained within matrix (810), which has been ingested by the patient, and thereafter, detector (802) receives beam (804) after having interacted with the reagent in matrix (810). It will be appreciated that such a reagent may be either injected or swallowed by the user prior to using source (806) and detector (802). In the illustrated version, a top compression plate (814) and bottom compression plate (816) are used to compress finger (812), but it will be appreciated that compression plates (814, 816) need not necessarily be used.

Figure 10:
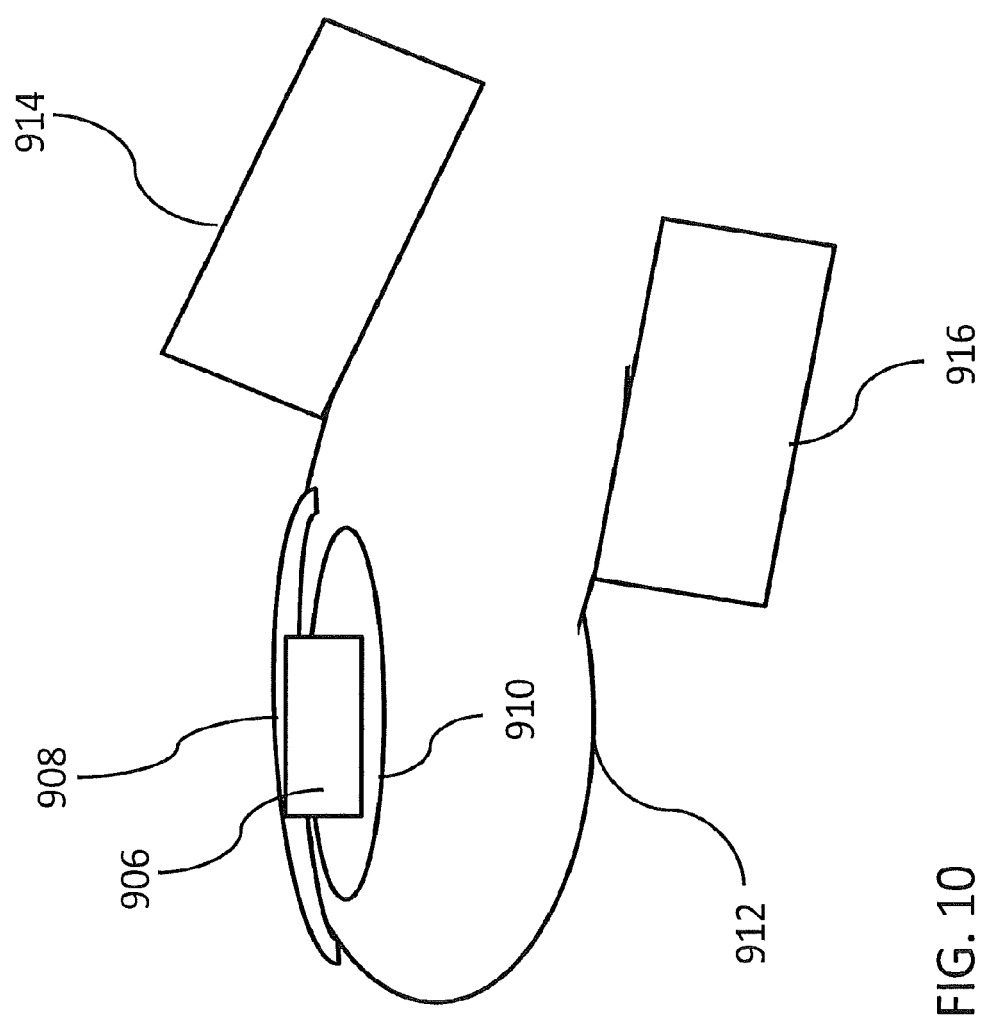
FIG. 10 depicts a side elevation view of yet another alternative exemplary version of a source and a detector with compression plates at the rear of the finger.

FIG. 10 shows yet another different configuration for using compression plates (914, 916) with finger (912) where compression plates (914, 916) are positioned away from the end of finger (912). A source (906) is positioned to transmit a beam through nail (908) to intersect matrix (910) to be received by a detector (not shown). It will be understood that while the illustrated version shows compression plates (914, 916) to be positioned just behind nail (908), compression plates (914, 916) may be placed anywhere along finger (912). Furthermore, rather than being positioned above and below finger (912), compression plates (914, 916) may be placed at the sides of finger (912) in any suitable position. Furthermore, in some instances, rather than compression plates (914, 916), a compression ring or other compressing device may be used as would be apparent to one of ordinary skill in the art in view of the teachings herein.

Figure 15A:
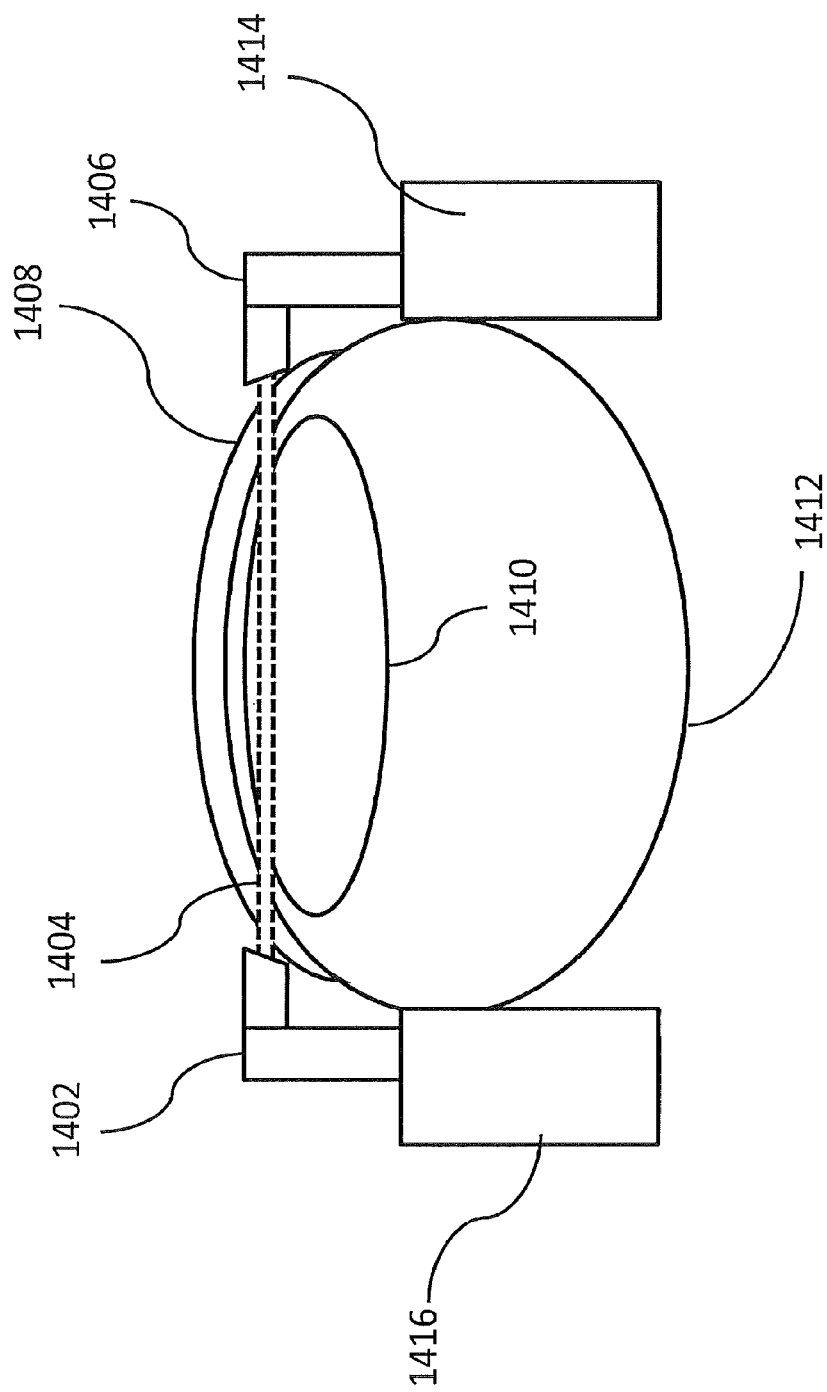
FIG. 15A depicts a front partially cross sectional view of yet another alternative exemplary version of a source and a detector having side compression plates.
Figure 15B:
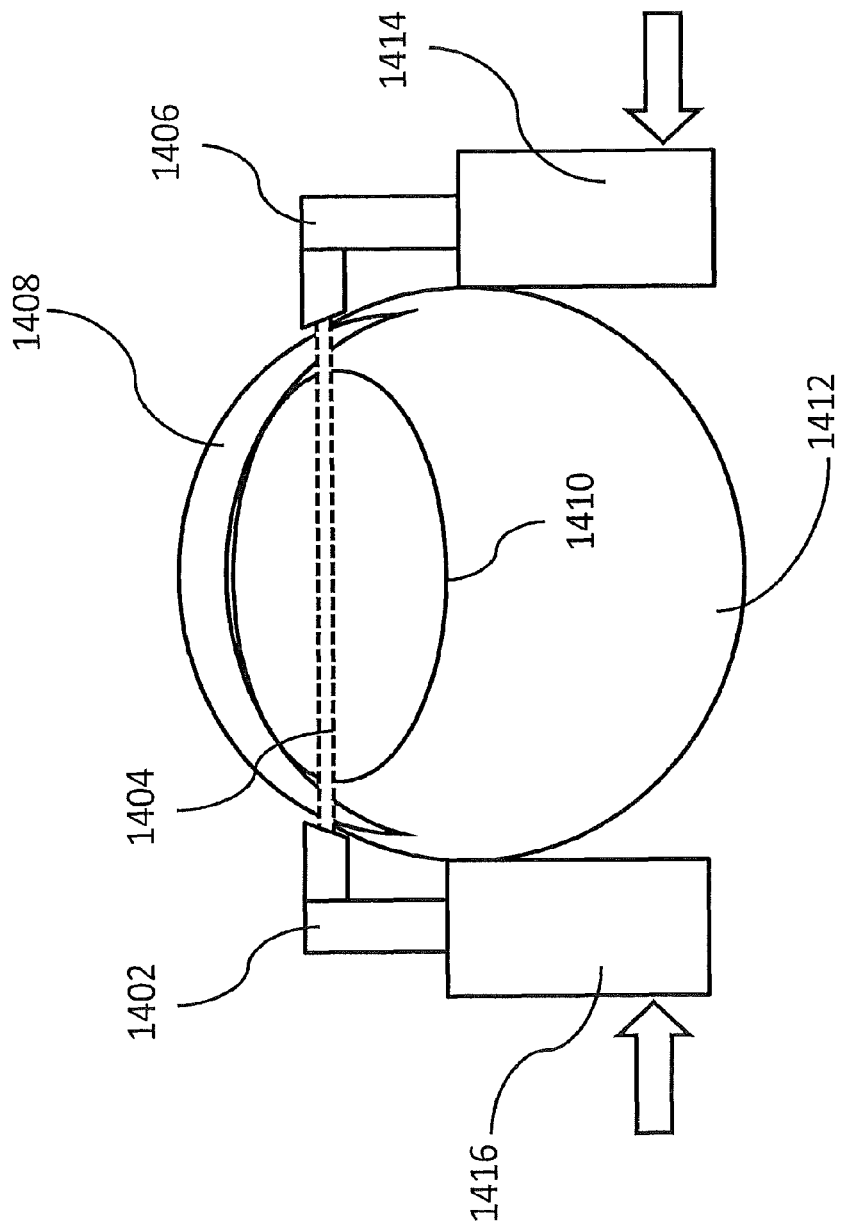
FIG. 15B depicts a front partially cross sectional view of the source and the detector of FIG. 15B with the side compression plates squeezing the finger.

FIGS. 15A and 15B shows yet another exemplary version where a source (1406) fires a beam (1404) laterally through nail (1408) into matrix (1410) such that detector (1402) receives beam (1404) after beam (1404) is transmitted, absorbed and emitted, refracted, scattered, or reflected by matrix (1410) and/or analytes contained within matrix (1410) of finger (1412). FIG. 15A shows side compression plates (1414, 1416) in an uncompressed state. FIG. 15B shows side compression plates (1414, 1416) squeezing finger (1412). As shown in the illustrated version, squeezing side compression plates (1416, 1416) compresses finger (1412) as well as bows nail (1408) upwards. It will be appreciated that it may be desirable to have nail (1408) bow upwards. For instance, beam (1404) may have a larger diameter when traveling through nail (1408) that has been bowed. It will also be appreciated that using side compression plates (1416, 1416) could assist the use of source (1406) and detector (1402) in patients having flatter nails (1408) that might otherwise be difficult to fire beam (1404) into nail (1408) laterally. Compressing finger (1412) may also increase or create different blood flow through finger (1412) that might be used to provide calibration or other relevant measurements.

Figure 11:
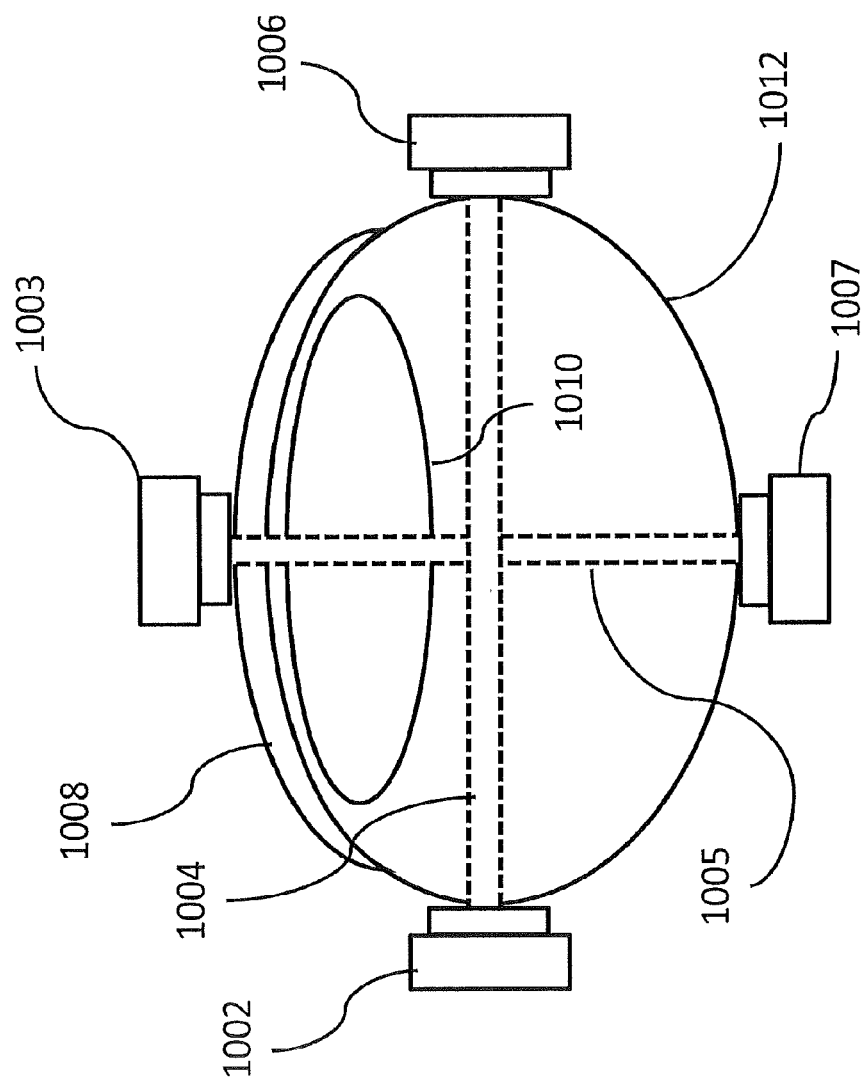
FIG. 11 depicts a front partially cross sectional view of yet another alternative exemplary version of a source and a detector oriented horizontally across a finger as well as a second source and detector oriented vertically across a finger.

FIG. 11 shows yet another version of a source (1006) positioned to fire a horizontal beam (1004) through finger (1012) to be received by detector (1002). A second source (1007) is positioned to fire a second beam (1005) vertically through finger (1012) to be received by a second detector (1003). It will be appreciated that first beam (1004) and second beam (1005) may intersect or may simply be positioned transversely without interrupting each other. While in the exemplary version, first beam (1004) passes through nail (1008) and matrix (1010), while second beam (1005) does not, it will be appreciated that second beam (1005) may be positioned to intersect matrix (1010) as well. Furthermore, while in the illustrated version, first beam (1004) and second beam (1005) pass through each other in a perpendicular manner, other non-perpendicular paths may be used as would be apparent to one of ordinary skill in the art in view of the teachings herein. It will further be appreciated that beams (1004, 1005) may be used in addition to the configuration shown, for instance, in FIG. 2, such that multiple beams of data are presented and collected. For instance, beam (1005) may be used to collect information with regard to the physiology of finger (1012) whereas beam (1004) could be used to collect information regarding analytes in matrix (1010) of finger (1012). In such an implementation, the physiological information could be recorded or otherwise monitored alongside the analyte information allowing the user to see how they relate or otherwise affect each other.

Figure 12:
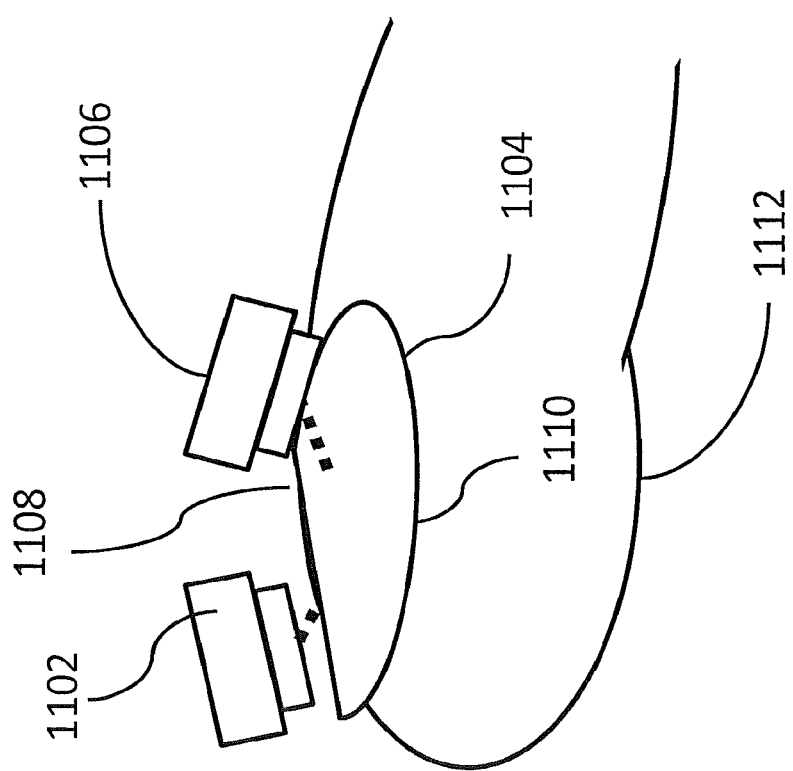
FIG. 12 depicts a side elevation view of yet another alternative exemplary version of a source and a detector with the source and the detector positioned on the nail of a finger.

FIG. 12 shows yet another alternative version of source (1106) and detector (1102). Source (1106) fires a beam (1104) through nail (1108) into matrix (1110). As seen in the illustrated version, beam (1104) is fired laterally through into matrix (1110). It will be appreciated that at least a portion of beam (1104) may be scattered or otherwise reflected such that detector (1102) receives a portion of beam (1104) as it scatters or reflects off matrix (1110). As can be seen in FIG. 12, source (1106) and detector (1102) may be positioned along top of nail (1108). It will be appreciated that source (1102) may be positioned anywhere along the top of nail (1108) such that source (1102) fires horizontally or laterally into nail (1108) as would be apparent to one of ordinary skill in the art in view of the teachings herein.

Figure 13:
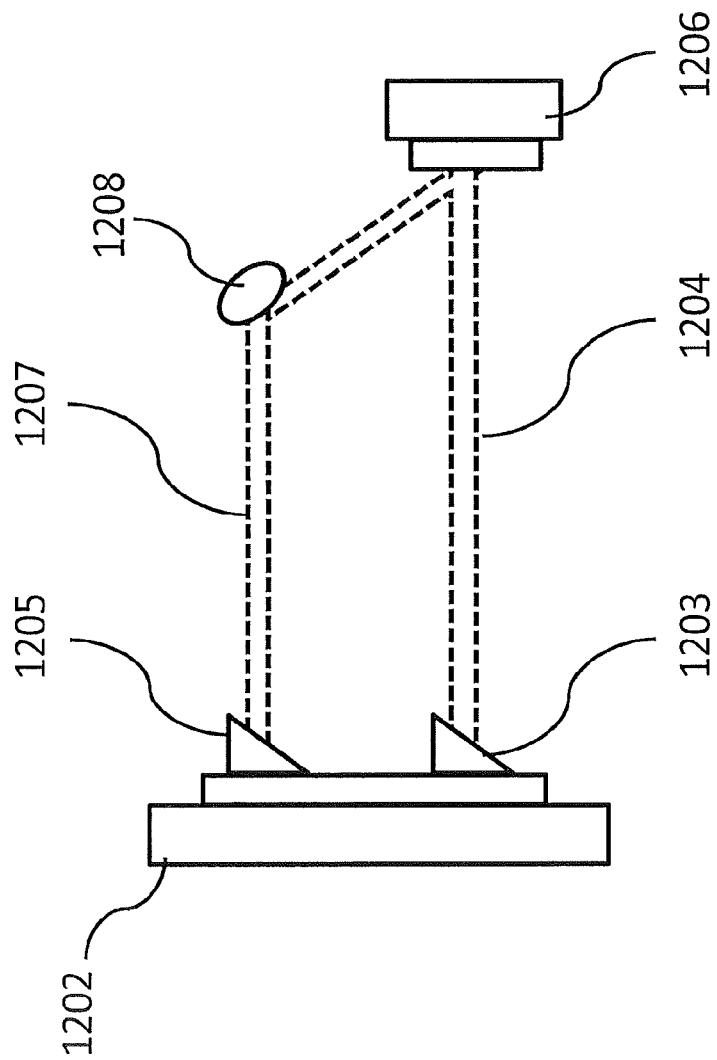
FIG. 13 depicts a front elevation view of an alternative exemplary version of a source and a detector operable to deliver a split beam.

FIG. 13 shows an alternative source (1206) and detector (1202), which may be used in any of the configurations shown above in FIGS. 1-12. Source (1206) is operable to project a beam (1204) through a nail (not shown) to determine the presence and/or concentration of an analyte. Detector (1202) comprises a first sensor (1203) and a second sensor (1205). First sensor (1203) and second sensor (1205) are positioned such that first sensor (1203) receives a portion of beam (1204) directly from source (1206) and second sensor (1205) receives a spread portion of beam (1207) that reflects off of reflector (1208). Alternatively, source (1206) may be operable to transmit a split beam (1204, 1207) for traveling through a finger to be directed toward detector (1202). Other configurations will be apparent to one of ordinary skill in the art in view of the teachings herein.

Figure 14:
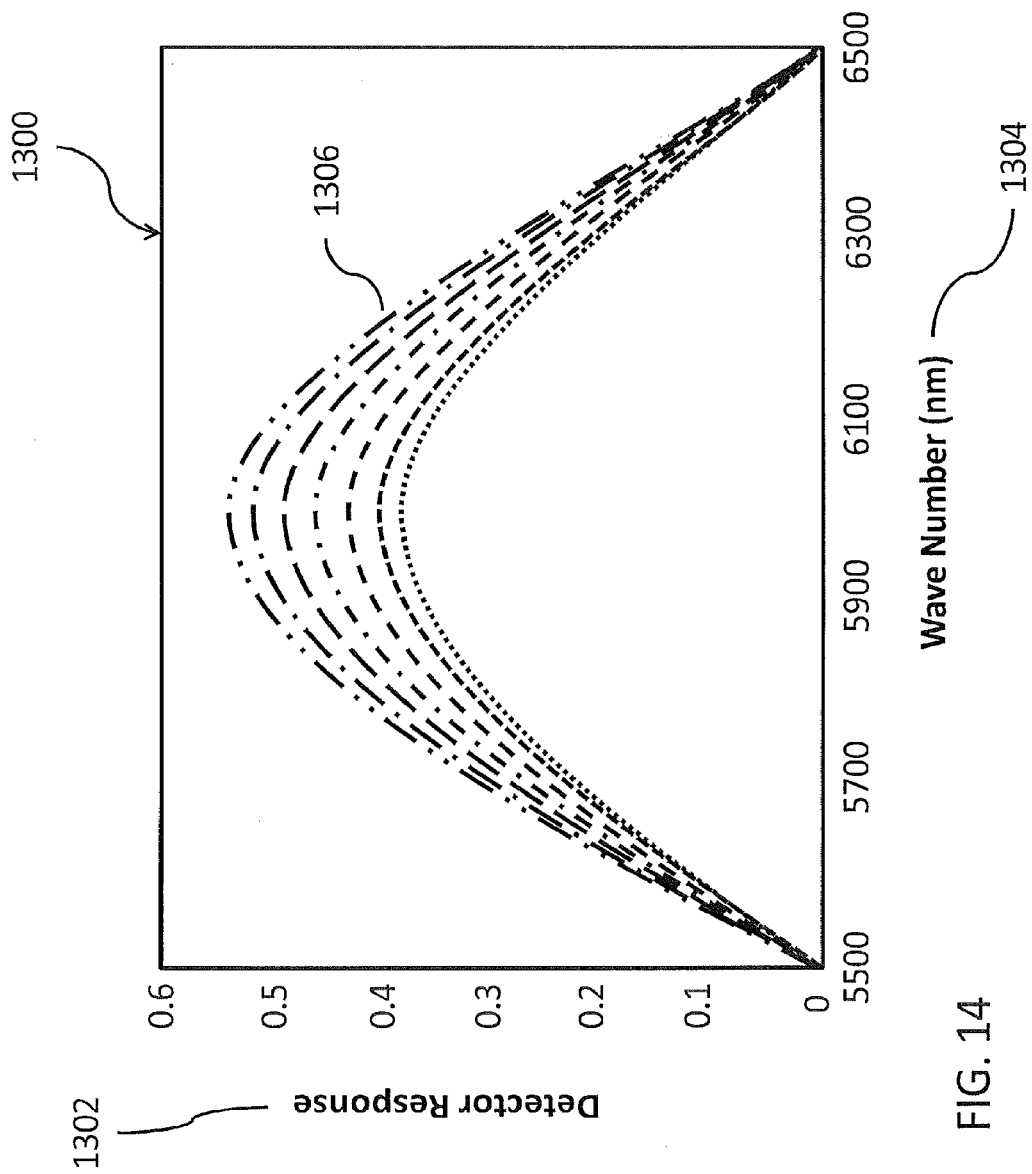
FIG. 14 depicts a chart view of potential readings from a detector.

Once a signal and/or light are received by a detector, such as any of the detectors shown in FIGS. 1-13, it will be understood that the signal received may be analyzed to determine the presence of analyte in the blood. As can be seen in FIG. 14, lines (1306) represent strength of responses based on various wave spectrums fired through a fingernail with different blood glucose concentrations. As shown in this illustrated version, the detector response (1302) is proportional to the analyte concentration. Given the intensity of response from 5900-6100 a line source with any of these wavelengths could be used to accurately measure analyte concentrations. Whether a broad source or single wavelength source, it will be appreciated that, other suitable signal analysis may be performed on the readings from detector as would be apparent to one of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of detecting an analyte using a source and a detector, wherein the source is operable to transmit a focused light beam to the detector, the method comprising the steps of:
   (a) placing the source on one portion of a nail of a human digit;
   (b) placing the detector on another portion of the nail;
   (c) firing the focused light beam through the nail toward the detector along a line defining a secant with the nail;
   (d) receiving at least a portion of the focused light beam with the detector;
   (e) processing a signal resulting from the receiving to detect an analyte.

2. The method of claim 1,
   wherein the source comprises a first collimator positioned to create the focused light beam, where the focused light beam has a path; and
   further comprising a second collimator positioned along the path of the focused light beam before the focused light beam reaches the detector.

* * * * *